US008775199B2

(12) United States Patent
Yan et al.

(10) Patent No.: US 8,775,199 B2
(45) Date of Patent: Jul. 8, 2014

(54) METHOD AND SYSTEM FOR IMAGE PUMPING

(75) Inventors: Yulong Yan, Little Rock, AR (US); Xuejun Weng, Little Rock, AR (US); Vaneerat Ratanatharathorn, Little Rock, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 1522 days.

(21) Appl. No.: 11/903,866

(22) Filed: Sep. 25, 2007

(65) Prior Publication Data

US 2009/0080721 A1 Mar. 26, 2009

(51) Int. Cl.
G06Q 10/00 (2012.01)
G06Q 50/00 (2012.01)
G06K 9/00 (2006.01)
G06F 19/00 (2011.01)

(52) U.S. Cl.
CPC ............................. *G06F 19/321* (2013.01)
USPC .................................. 705/2; 382/128

(58) Field of Classification Search
CPC ....................................................... G06F 19/00
See application file for complete search history.

(56) References Cited

U.S. PATENT DOCUMENTS

| 6,595,921 | B1* | 7/2003 | Urbano et al. | 600/437 |
| 6,943,909 | B2 | 9/2005 | Goldstein et al. | |
| 7,117,256 | B1 | 10/2006 | Blinn | |
| 7,339,183 | B1* | 3/2008 | Hecker et al. | 250/583 |
| 7,438,685 | B2 | 10/2008 | Burdette et al. | |
| 7,684,647 | B2 | 3/2010 | Fu et al. | |
| 7,693,257 | B2 | 4/2010 | Allison | |
| 2004/0122719 | A1* | 6/2004 | Sabol et al. | 705/7 |
| 2008/0052313 | A1* | 2/2008 | Keen | 707/104.1 |
| 2008/0082966 | A1* | 4/2008 | Dorn et al. | 717/120 |

OTHER PUBLICATIONS

Rorden, Chris, "The Dicom Standard" as obtained from the Intenet http://www.sph.sc.edu/comd/rorden/dicom.html.*
Scanning, definition, S.M.H. Collin 2002.*
3$^{rd}$ pty NPL submissions.*
JPEG—definition, downloaded from free online dictionary Jun. 21, 2010.*
Rorden, Chris, "The Dicom Standard," as obtained from the Internet http://sph.sc.edu/comd/rorden/dicom.html used as definition. Download date Nov. 20, 2009.*

* cited by examiner

*Primary Examiner* — Neal Sereboff
(74) *Attorney, Agent, or Firm* — J. Charles Dougherty (57) ABSTRACT

A method and system to "pump" radiation therapy (RT) images and associated patient information on an Image Guided Radiation Therapy (IGRT) system to a Record and Verify (R&V) system via a standard DICOM connection to allow remote image viewing. Targeted image files in IGRT systems are searched for and transferred automatically. The user identifies the "inlet," i.e. the source from which the image files are searched, and the "outlet," i.e., the DICOM server to which the "pumped" imaged are directed. The images can be sent in their original form or fused. The "input" source is scanned periodically at a user-determined time interval. In order not to send the same image multiple time, a time filter skips images generated before a user-selected time and date.

9 Claims, 8 Drawing Sheets

METHOD AND SYSTEM FOR IMAGE PUMPING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to radiotherapy imaging systems, and in particular, to a method and system for automatic radiation therapy (RT) image transfer between Image Guided Radiation Therapy (IGRT) systems and Record and Verify (R&V) systems.

2. Brief Description of the Related Art

Image Guided Radiation Therapy (IGRT) is the next-generation of technology for high precision radiotherapy. The X-Ray 6D IGRT system sold by BrainLAB under the trademark ExacTrac® is an example of an automated IGRT system. It utilizes high-resolution kV x-rays to image the targets before treatment, registers the in-room images with the planning images to determine the degree of shifts needed for perfect alignment, robotically corrects patient set-up errors and track any patient and/or target movement throughout the treatment, all within a standard treatment time slot. However, this system lacks the ability to communicate with a Record and Verify (R&V) system in a radiation therapy clinic.

The limitations of the prior art are overcome by the present invention as described below.

BRIEF SUMMARY OF THE INVENTION

The present invention is a method and system that "pumps" radiation therapy (RT) images, particularly JPEG format images, from an IGRT system to an R&V system via a DICOM connection to allow remote image viewing. DICOM ("Digital Imaging and Communications in Medicine") is a standard that is designed to ensure that systems are interoperable to display, send, store and process medical images and derived documents.

Even if the IGRT system does not allow remote reviewing of images on other systems, the method and system of the present invention allows remote reviewing of images via a DICOM connection and in addition transfers intact all original patient information from the IGRT system. Although the method and system of the present invention is a solution to the problem of communication of RT images from an ExacTrac® IGRT system to R&V systems, the present invention is not limited thereto.

The method and system of the present invention searches for targeted image files in IGRT systems and transfers them automatically to remote R&V systems via a standard DICOM connection. The user identifies the "inlet," i.e. the source from which the image files are searched, and the "outlet," i.e., the DICOM server to which the "pumped" images are directed. The images can be sent in their original form or fused.

The method and system of the present invention scans the "input" source periodically at a user-determined time interval. In order not to send the same image multiple times, a time filter skips images generated before a user-selected time and date.

The method and system of the present invention combines radiographic information with textual information from log files in the targeted system and presets in the current system to encode DICOM images so that they are associated with patients automatically when sent to an R&V system. No human intervention is needed.

The method and system of the present invention utilizes a sentinel module to probe the presence of the targeted source and the destination and to signal their states to the user. It hibernates when either the targeted source or the destination DICOM server is not available and resumes working status when both "inlet" and "outlet" become available.

The method and system of the present invention finds paired DRR images and x-ray images and sends fused ones to an R&V system via a DICOM connection so that quantitative estimation of image registration accuracy becomes feasible.

These and other features, objects and advantages of the present invention will become better understood from a consideration of the following detailed description of the preferred embodiments and appended claims in conjunction with the drawings as described following.

BRIEF DESCRIPTION OF THE SEVERAL VIEWS OF THE DRAWINGS

FIG. 9 is a view of a GUI, specifically a dialog box, of an embodiment of the image pumping system of the present invention by which the user is able to view a log of the system activity.

DETAILED DESCRIPTION OF THE INVENTION

With reference to FIGS. 1-12, the preferred embodiments of the present invention may be described.

Image Guided Radiation Therapy (IGRT) is the next-generation of technology for high precision radiotherapy. An IGRT system 10 utilizes high-resolution kV x-rays to image the targets before treatment, registers the in-room images with the planning images to determine the degree of shifts needed for perfect alignment, corrects patient set-up errors and tracks any patient and/or target movement throughout the treatment.

Figure 1:
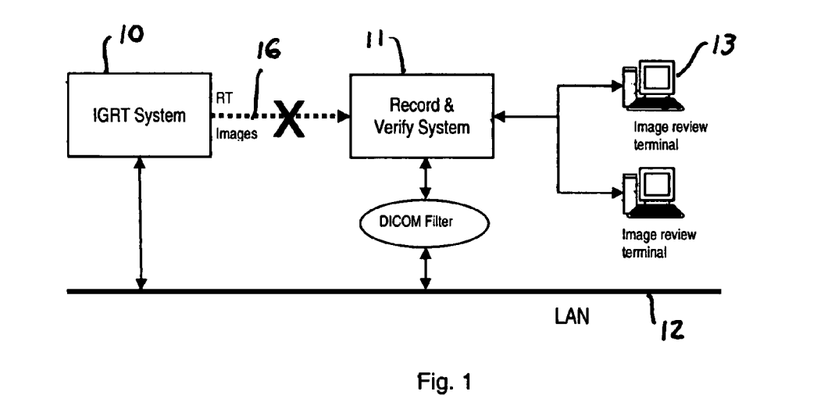
FIG. 1 is a block diagram of an IGRT system and an R&V system without the image pumping system of the present invention.

However, if, as FIG. 1 illustrates, the IGRT system 10 lacks the ability to communicate with a Record and Verify (R&V) system 11 in a radiation therapy clinic, the users will be inconvenienced in reviewing images through a local area network (LAN) 12 on an image review terminal 13 and lose many of the advantages of working in a digital environment.

Figure 2:
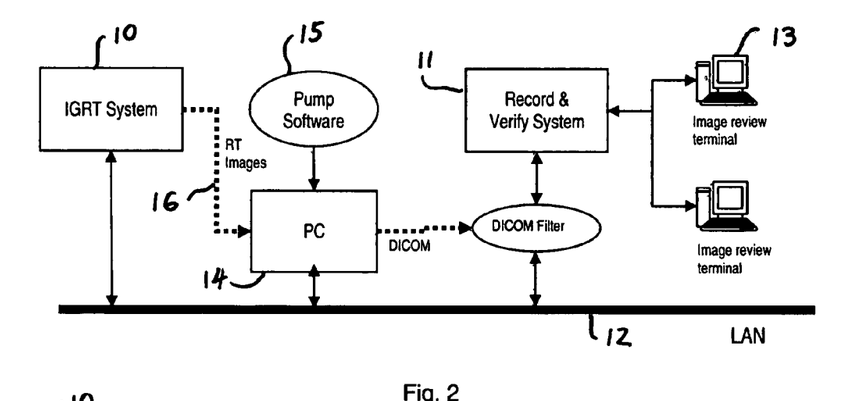
FIG. 2 is a block diagram illustrating an embodiment of the image pumping system of the present invention remotely installed on a data processing device separate from the IGRT system.
Figure 3:
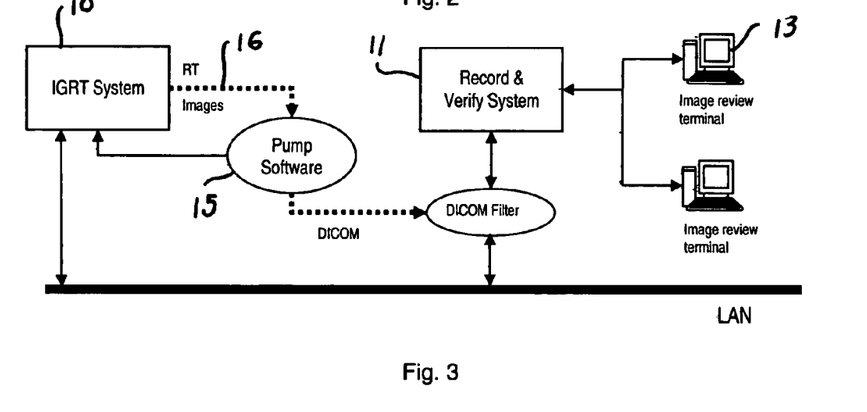
FIG. 3 is a block diagram illustrating an embodiment of the image pumping system of the present invention locally installed on a data processing device associated with the IGRT system.

The present invention is a method and system that bridges the gap between an incompatible IGRT system 10 and an R&V system 11 by pumping radiation therapy (RT) images 16, particularly JPEG images, including both digitally reconstructed radiographs (DRR) or kV x-ray images, from a local or remote IGRT system 10 to an R&V system 11. The system 15 of the present invention may reside on a remote data processing device 14 separate from the IGRT system as shown in FIG. 2 or may reside on a data processing device associated with the IGRT system itself as shown in FIG. 3. The system 15 is preferably compliant with the Digital Imaging and Communication in Medicine (DICOM) standard, which is widely accepted in healthcare systems all over the world.

All original patient data (for example, files F1-F3 in FIG. 4) 20 on the IGRT system 10 is communicated intact along with the RT images 16. Radiographic information is combined with textual information from log files in the targeted system and presets in the current system to encode DICOM images so that they are associated with patients automatically when sent to an R&V system. No human intervention is needed. The system 15 may be modified to run on any data processing device. The preferred embodiments will run in a standard PC operating environment with read access privilege to the patient data directory 21 on the data processing device associated with the IGRT system 10. Desirably the system 15 runs fully automated in the background without interfering with any clinical work on the data processing device on which it is installed.

The system of the present invention may be installed as an application on a data processing device by creating a directory as the home directory for the application where an executable (".exe") file is placed. This file will look for an ".ini" file the first time it runs. This is a configuration file containing license and initialization parameters, such as the source IGRT patient directory and the receiving DICOM server. It will also create a subdirectory "log" for the daily log file as described below.

Another configuration file, "dicom_server.cfg," contains information about all DICOM servers to which the application can send RT images 16. The user 22 must provide information concerning the receiving DICOM servers. Setting up a receiving DICOM server is described in more detail below with respect to FIG. 7.

A sentinel module is utilized to probe for the presence of the targeted source and the destination and to signal their states to the user. The system hibernates when either the targeted source or the destination DICOM server is not available and resumes working status when both "inlet" and "outlet" become available.

Figure 5:
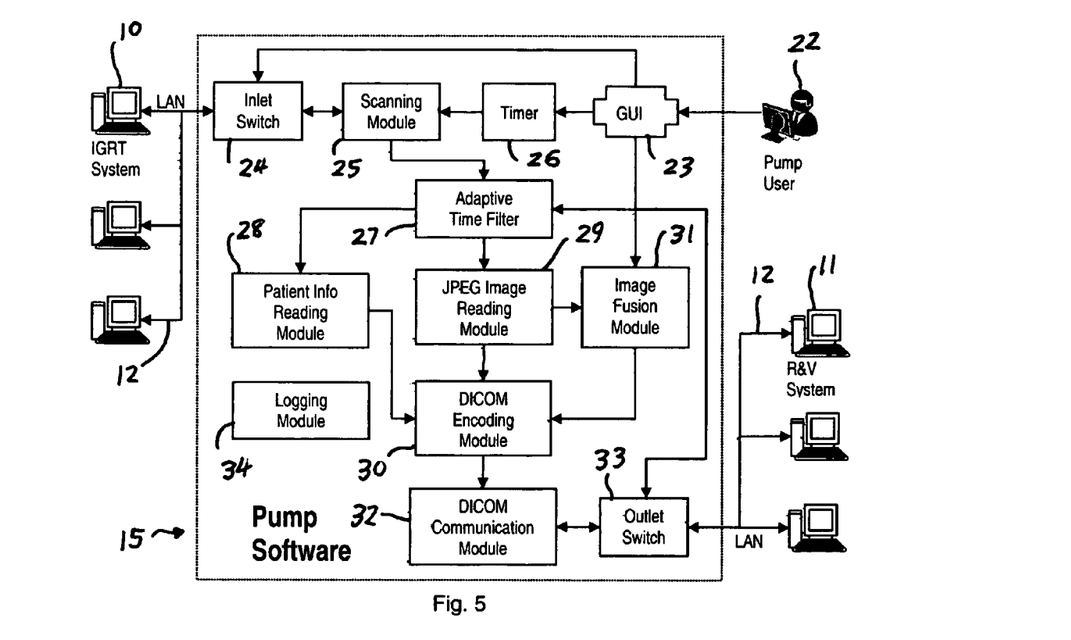
FIG. 5 is block diagram of an embodiment of the present invention illustrating the interaction of the several modules of the image pumping method and system of the present invention.

As shown in FIG. 5, the system 15 of the present invention comprises several modules which are accessed and controlled by the user 22 through a graphical user interface (GUI) 23. The inlet switch module 24 selects the IGRT system 10 from which RT images 16 are pumped via a local area network (LAN) 12. The scanning module 25 periodically scans the files on the inlet IGRT system 10 for RT images 16. The time interval is determined by the timer module 26. Further, the adaptive time filter module 27 determines those RT image files whose creation precedes a selected time and date. The patient information reading module 28 retrieves intact all patient information associated with the pumped RT images 16. The JPEG image reading module 29 reads the JPEG format RT images 16 and transfers them to the DICOM encoding module 30 or to the image fusion module 31 if fused images are selected. The DICOM encoding module 30 encodes the JPEG format RT images 16 into DICOM format and provides the DICOM encoded images to the DICOM communications module 32, which ensures that the images are compliant with the DICOM communications standards. The RT images 16 are then sent by the outlet switch module 33 to the selected R&V system 11 over a local area network (LAN) 12. The logging module 34 logs all system activity.

Figure 6:
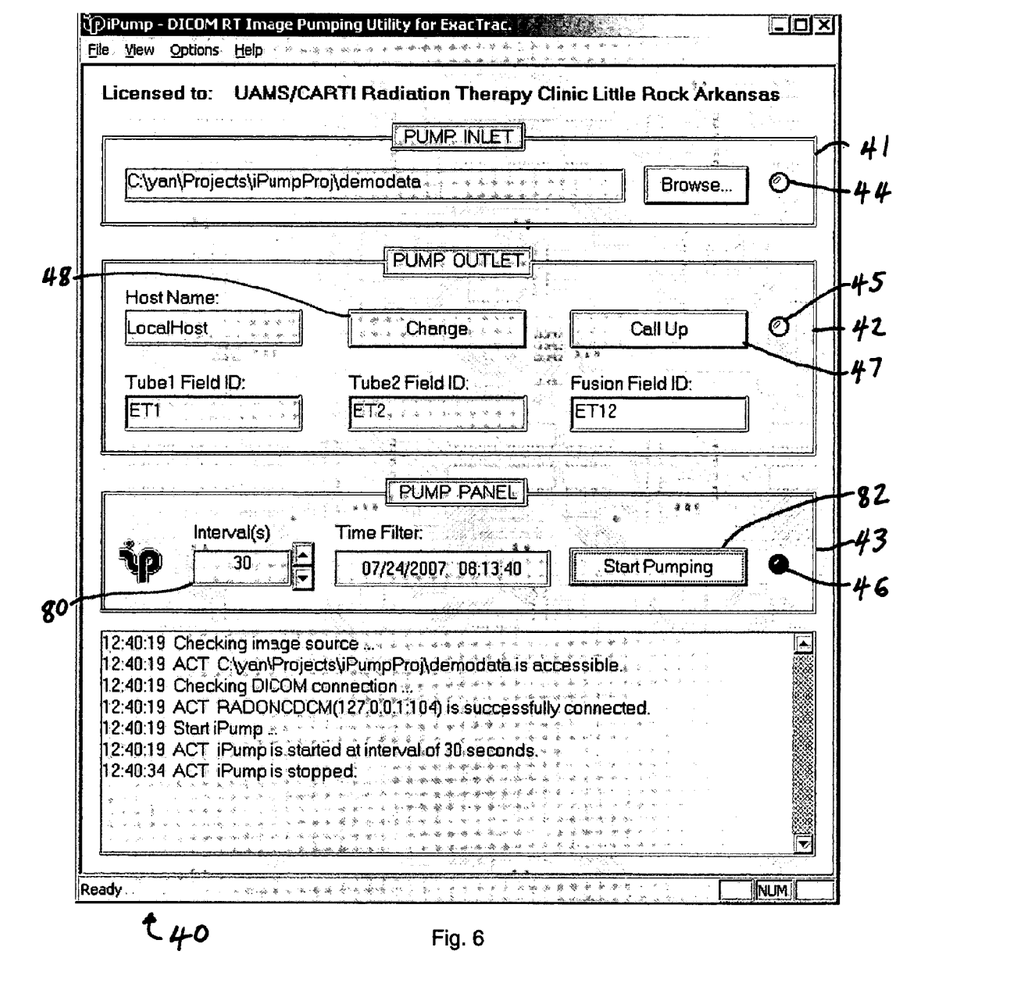
FIG. 6 is a view of a graphical user interface (GUI), specifically the main window, of an embodiment of the image pumping system of the present invention by which the user sets the image source (pump inlet), image destination (pump outlet), periodic pumping interval and time filter.

The GUI module 23 presents a main window 40 as illustrated in FIG. 6 and related dialog boxes. The main window 40 is the major interactive window for routine use. Dialog boxes are designed for the purposes of system administration and maintenance as described below.

Since the system 15 works like a pump, the GUI main window 40 is configured analogously as shown in FIG. 6 with three sections: PUMP INLET 41, PUMP OUTLET 42 and PUMP PANEL 43. Each section has an indicator 44, 45, 46 showing its working condition. The indicators 44, 45, 46 turn green when ready. Otherwise the indicators 44, 45, 46 are either red or yellow depending on the situation.

The PUMP INLET panel 41 selects the image source, which is the patient data directory on the mapped network drive on the data processing device associated with the selected IGRT system 10. As noted above, the sentinel module (not shown) of the system 15 checks its accessibility periodically. When the indicator 44 turns red, the IGRT system 10 has been turned off.

A red signal on the indicator 44 does not stop the system 15 nor does the user 22 have to close it. The system 15 will continue working in the background checking the image source identified by the PUMP INLET 41 periodically and will resume pumping when the IGRT system 10 is turned on again and the image source selected from the PUMP INLET 41 is ready.

The PUMP OUTLET 42 selects the receiving DICOM server. The system 15 requires the AE (Application Entity) title, IP address and port number of that server. The user 22 may click the "Call Up" button 47 to test the connection. That is the only button that prevents the system 15 from working if a DICOM connection is not available. When the indicator 45 turns green, it is ready to return to the main window PUMP PANEL section 43.

Figure 7:
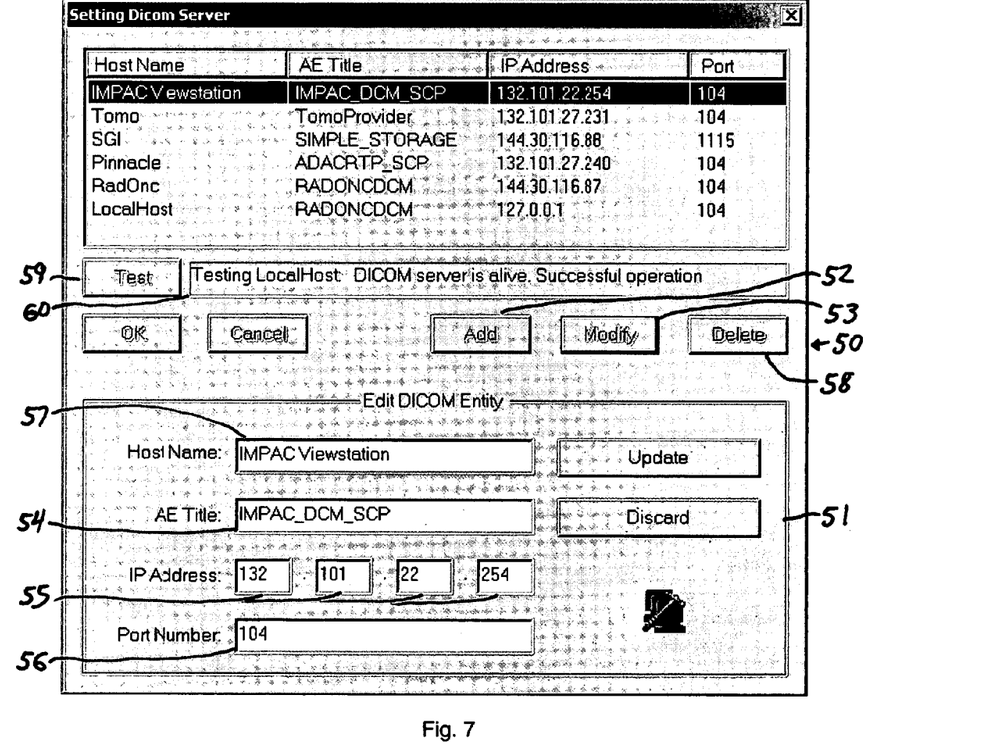
FIG. 7 is a view of a GUI, specifically a dialog box, of an embodiment of the image pumping system of the present invention by which the user sets the DICOM server.

As noted above, information concerning the DICOM destination server is saved in an ".ini" file and is read automatically when the system 15 starts. For routine use, the user 22 does not have do anything but verify that the DICOM destination server is correctly identified. If the destination DICOM server has to be changed for some reason, the "Change" button 48 may be used. FIG. 7 shows the dialog box 50 that pops up when the "Change" button 48 is clicked. The dialog box 50 may displayed in a expanded form or in a compact form depending on the functions being activated. The expanded form is shown in FIG. 7. The compact form would not include the "Edit DICOM Entity" panel 51.

The dialog box 50 is not only a DICOM server selection tool, but also an administrative tool for setting the DICOM servers. When the "Add" button 52 or "Modify" button 53 is pressed, the dialog box 50 expands to its expanded form as shown in FIG. 7 and allows the user 22 to enter or edit parameters for a new or modified DICOM server.

As mentioned above, a DICOM server is identified by the Application Entity (AE) title 54, IP address 55 and port number 56. The hostname 57 is a more readable expression of IP address. For example, the hostname as shown in FIG. 7 may refer to the IMPAC Viewstation, an R&V system sold by IMPAC Medical Systems, Inc., or, as "Pinnacle," to the 3D radiotherapy treatment planning system sold by ADAC Laboratories under the trademark Pinnacle3®. In the dialog box 50, the user 22 can also delete DICOM entities by using the "Delete" button 58. The dialog box 50 is also equipped with a "Test" button 59 to test the network connection. A feedback message 60 is displayed next to the "Test" button 59.

Desirably, the system 15 is provided with built-in interlocks to avoid human errors such as mistyping, incomplete information and the like.

Figure 4:
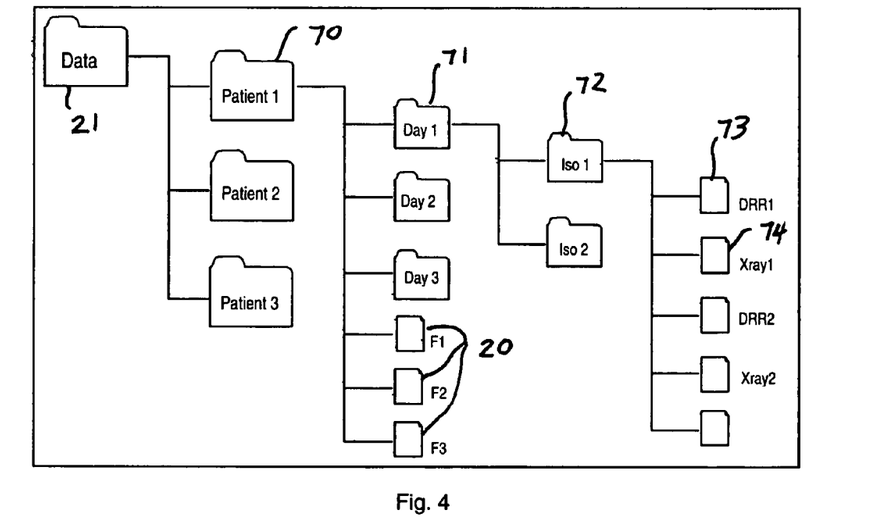
FIG. 4 is a block diagram illustrating a hierarchical file system on an IGRT system, such as the ExacTrac® IGRT system.

On the IGRT system sold by BrainLAB under the trademark ExacTrac®, patient data is stored in a hierarchical file arrangement as shown in FIG. 4. Each patient has a dedicated directory 70, in which all RT images are stored. The data files are further divided into subdirectories 71 of individual days, which might be further divided into multiple subdirectories 72 of multiple isocenters. In each directory for each corresponding isocenter, both DRR images 73 and x-ray images 74 of corrected and non-corrected positioning are stored in pairs. To facilitate more efficient scanning of the files, advantage can be taken of the hierarchical nature of the files. When a new folder is created, it is stamped with the date and time of creation. A hierarchical level of files may then be searched for the most recent date stamps that occur after the user-selected time and date. Lower levels of files associated with less recent date stamps may be bypassed so that the periodic searches are more efficient.

Pumped RT images 16 can be sent in two ways: original and fused. To send original images, the image pair option is enabled by checking menu item "Enable Pair Images" under menu "Options". One field is created for Tube 1, and the other is for Tube 2. Field ID's are determined by the user, for example, ET1 and ET2. Four images will be sent to the R&V system 11 for each isocenter for each patient per fraction. To send fused images, the present invention finds paired DRR images and x-ray images and sends fused images to an R&V system via a DICOM connection so that quantitative estimation of image registration accuracy becomes feasible.

To facilitate image review, it is recommended that IGRT images (DRR 73 and x-ray 74) be associated with specially created fields with distinctive ID's. Those fields are not used for treatment. They are only used for the purpose of image review.

It is difficult, if not impossible, to compare the original image pair without a reference grid on or any overlapping reference image. So the system 15 of the present invention provides the user with the image fusion option (Option-Enable Fusion Images) mentioned above. The fusion image for Tube 1 is identified as "Portal" while the fusion image for Tube 2 is identified as "DRR" to facilitate image review. Two fusion images for two tubes will be sent to the R&V system 11 for each isocenter of each patient per fraction.

If the IGRT system 10 does not provide updated information each time an RT image 16 is taken, for instance, in a general log file, the system 15 must scan the patient directory periodically at defined intervals. As shown in FIG. 6, the unit for the defined interval 80 may be in seconds and the range is desirably from 1 through 120 seconds. A scanning interval of 20-40 seconds is preferred.

Figure 8:
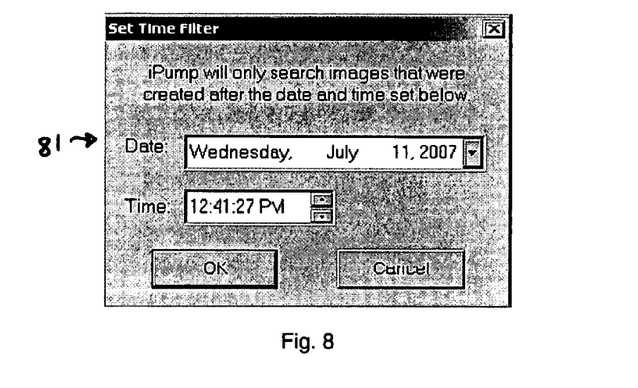
FIG. 8 is a view of a GUI, specifically a dialog box, of an embodiment of the image pumping system of the present invention by which the user modifies the time filter.

In order not to send the same image multiple times, the system 15 uses an adaptive time filter 27 to skip images generated before a user selected time and date. The adaptive time filter 27 is set in the dialog box 81 as shown in FIG. 8. The dialog box 81 is accessed by menu item "Change Time Filter" under menu "Options". The time filter is adaptive in that it may continually update the time and date based on its image scan to select only the most recent images. The user 22 may also override the time filter 27 in order to pick up images occurring after some earlier time and date, for example at a point in time where the user has previously discontinued reviewing images.

Time filtering can be disabled by unchecking menu item "Enable Time Filter" under menu "Options". In this status, the system 15 scans the entire patient database and sends all found images to the DICOM server regardless of the time when they were generated.

The "Start Pumping" button 82 as shown in the main window 40 of FIG. 6 is the button to switch ON/OFF the application. When it is on, the indicator 46 turns from red to green.

In order not to interfere with other work on the host computer, the system 15 is desirably minimized into a dynamic icon in the task tray by clicking the minimization system icon on the title bar or the task tray icon. A full display reappears when the icon is clicked again. When it is not at working status, the icon may indicate the status by turning gray. When the cursor is moved over this icon, it will display the prompt message. When it is working, the tray icon will become another color, such as light blue. When the application is busy, the tray icon indicates the busy status by changing color, for example dark red. There is a pop-up menu associated with the task tray icon. It can be accessed by right-clicking on the icon.

The system 15 logs all activity in daily log files as shown in the log viewer 90 of FIG. 9. The daily log files are saved in the "log" subdirectory. In a log file, each line is a message. For example, 12:39:06 ACT RADONCDCM(127.0.0.1:104) is successfully connected.

Each such message consists of three fields: time, action code and action details. Users can open them in any text editor, Notepad for instance, and search for desired information.

SUMMARY OF ACTION CODES

1. SND SeNDing image to a receiving DICOM destination.
2. STA application was STArted.
3. EXT application was closed (EXiT).
4. ACT Miscellaneous ACTions.
5. ADM ADMinistrative action such as changing scanning interval or other system options.
6. ERR ERRors.

To facilitate retrospective data analysis or system maintenance, the user 22 can access the built-in log viewer 90 by clicking menu item "Log View" under menu "Options".

The user 22 can date range using the start date button 91, end date button 92 and event type button on the log viewer 90. The event type is categorized as follows: Action code 1 (SND) is selected using the "Image" event button 93, action codes 2 through 5 are selected using the "Admin" event button 94, and action code 6 (ERR) is selected using the "Error" event button 95.

The following scenario is one in which the user 22 might be using the log function in a clinic: the user 22 wants to know how many images were sent to an R&V system in the last week. All the user needs to do is to specify the date range using the start date button 91 and the end date button 92, select the "Image" category using the buttons 93, 94, 95 and click the "Print Log" button 96.

The system 15 does not send the log file to a printer directory, instead it pops up a word processor such as Notepad with log information in it. By doing this, the sorted log file can either be saved to a text file or be printed from within the word processor.

The system 15 is preferably fully compatible with the DICOM standard. The system 15 has been validated for the IMPAC R&V system, version 8.3, sold by IMPACT Medical Systems, Inc. The system 15 is anticipated to work with other versions of the IMPAC R&V system as long as RT images 16 are associated with a field ID. While the system 15 has only been validated for the IMPAC R&V system, version 8.3, it should be adaptable to other R&V systems.

Prior to sending a RT image 16 to an R&V system 11, the user 22 is advised to create setup fields for the IGRT system 10. Those fields are not for treatment but for images. The field ID is the only number the R&V system 11 is looking for.

To facilitate image reviewing for radiation oncologists, both the portal image and its reference image, usually a DRR, can be displayed side-by-side on the screen, provided they have been associated with the field either manually or automatically. Accordingly, the system 15 labels both DRR images and x-ray images of Tube 1 in "DRR", but "Portal" for those of Tube 2, in an attempt to display images from both tubes simultaneously on the screen.

The number of fields that must be created depends on how the system 15 is configured. In this regard, the system has two options to offer: Raw Images and Fused Images.

Field ET1. As the field ID implies, this field is created to "hold" raw images from Tube 1 of the IGRT system 10.

Field ET2. This field is created for holding raw images from Tube 2.

Field ET12 (recommended field ID). This field is created for holding fused images from both Tube 1 and Tube 2. As stated above, a fused image from Tube 1 is labeled "DRR", and that from Tube 2 is labeled "Portal".

Field ET1 and ET2 do not have to be created if the "Raw Images" option is not enabled. Also, field ET12 does not have to be created if the "Fused Images" option is not enabled.

Figure 10:
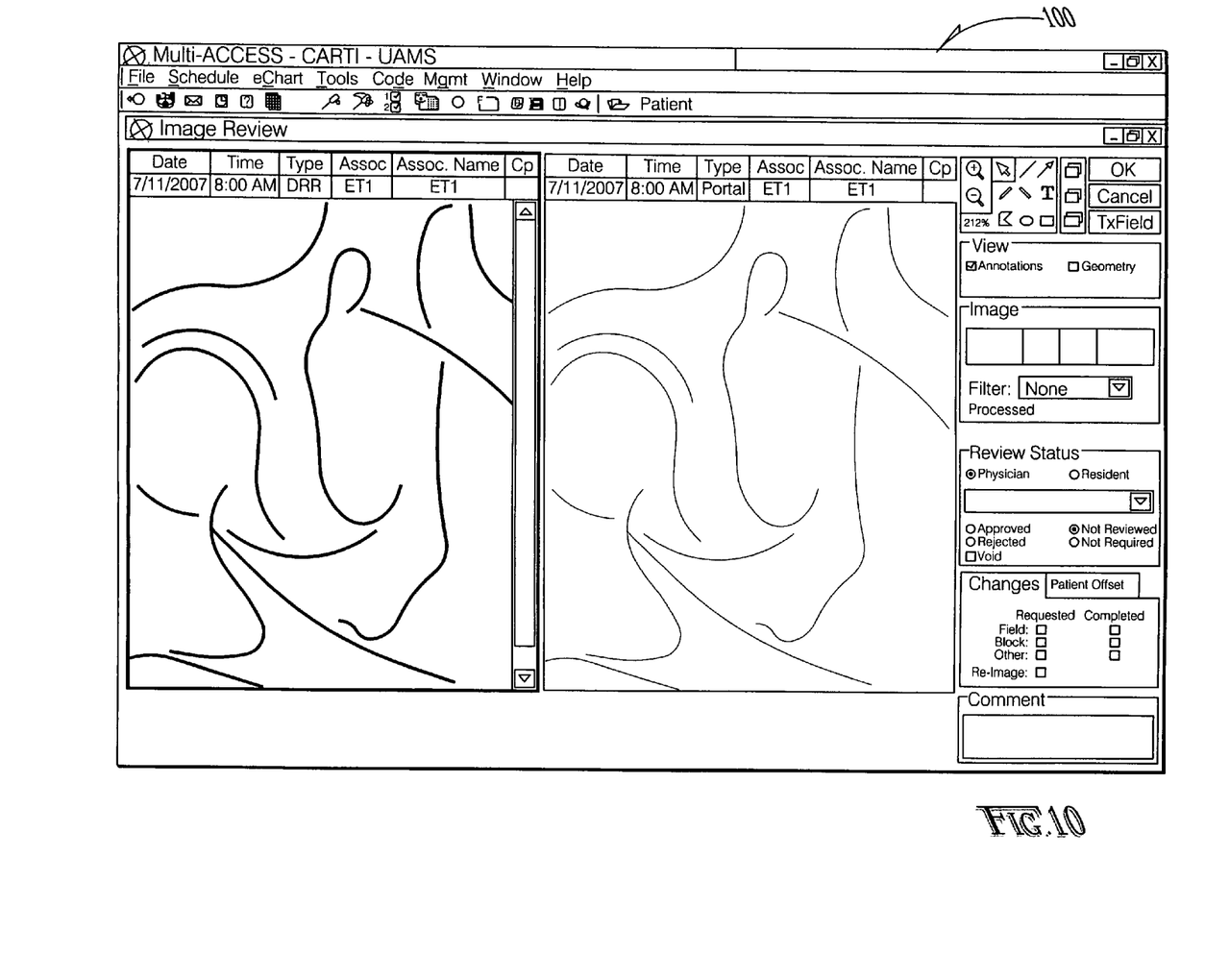
FIG. 10 is a view of a example R&V system showing a raw image review for Tube 1 where the left image is a DRR image and the right image is the corresponding x-ray image.
Figure 11:
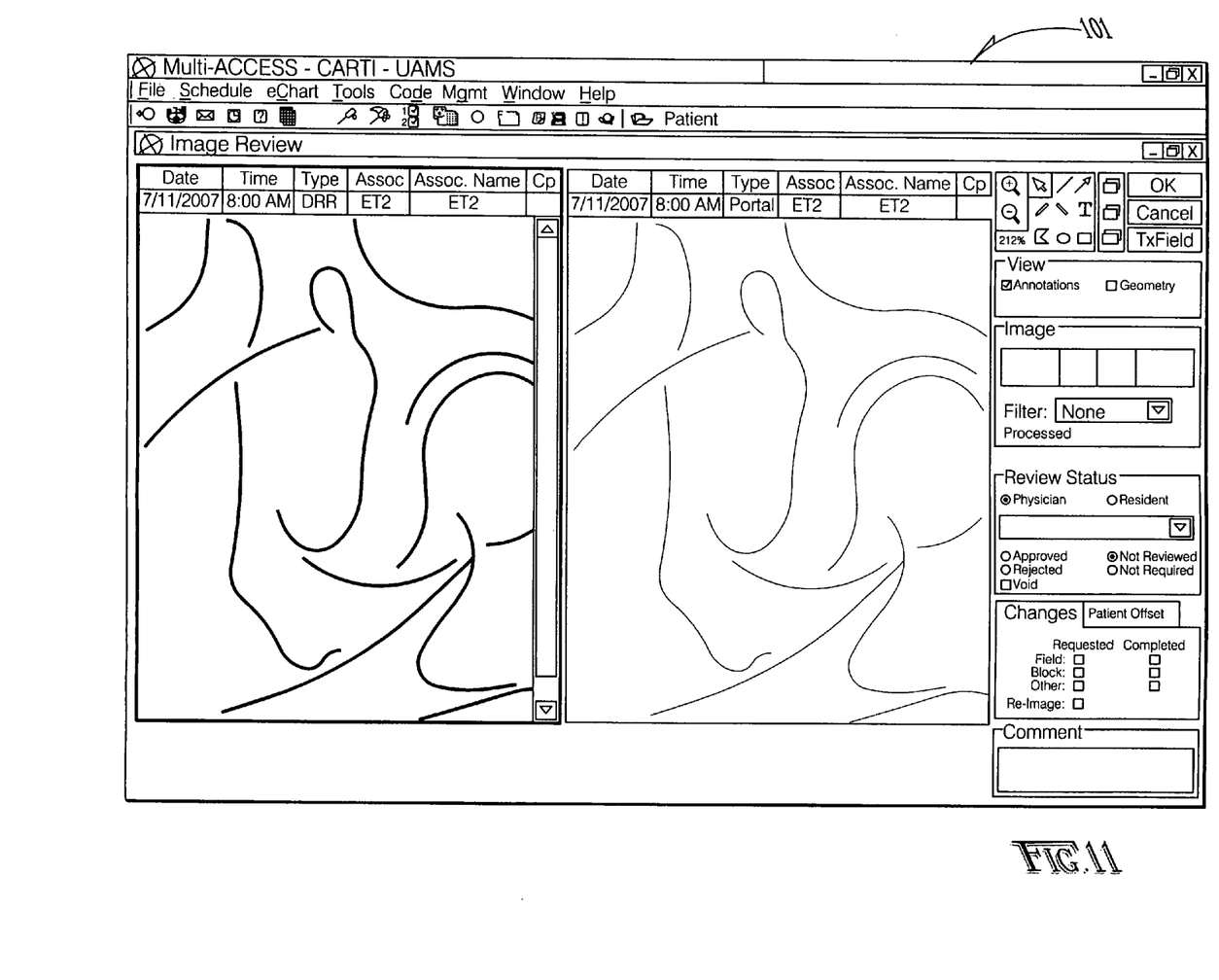
FIG. 11 is a view of a example R&V system showing a raw image review for Tube 2.
Figure 12:
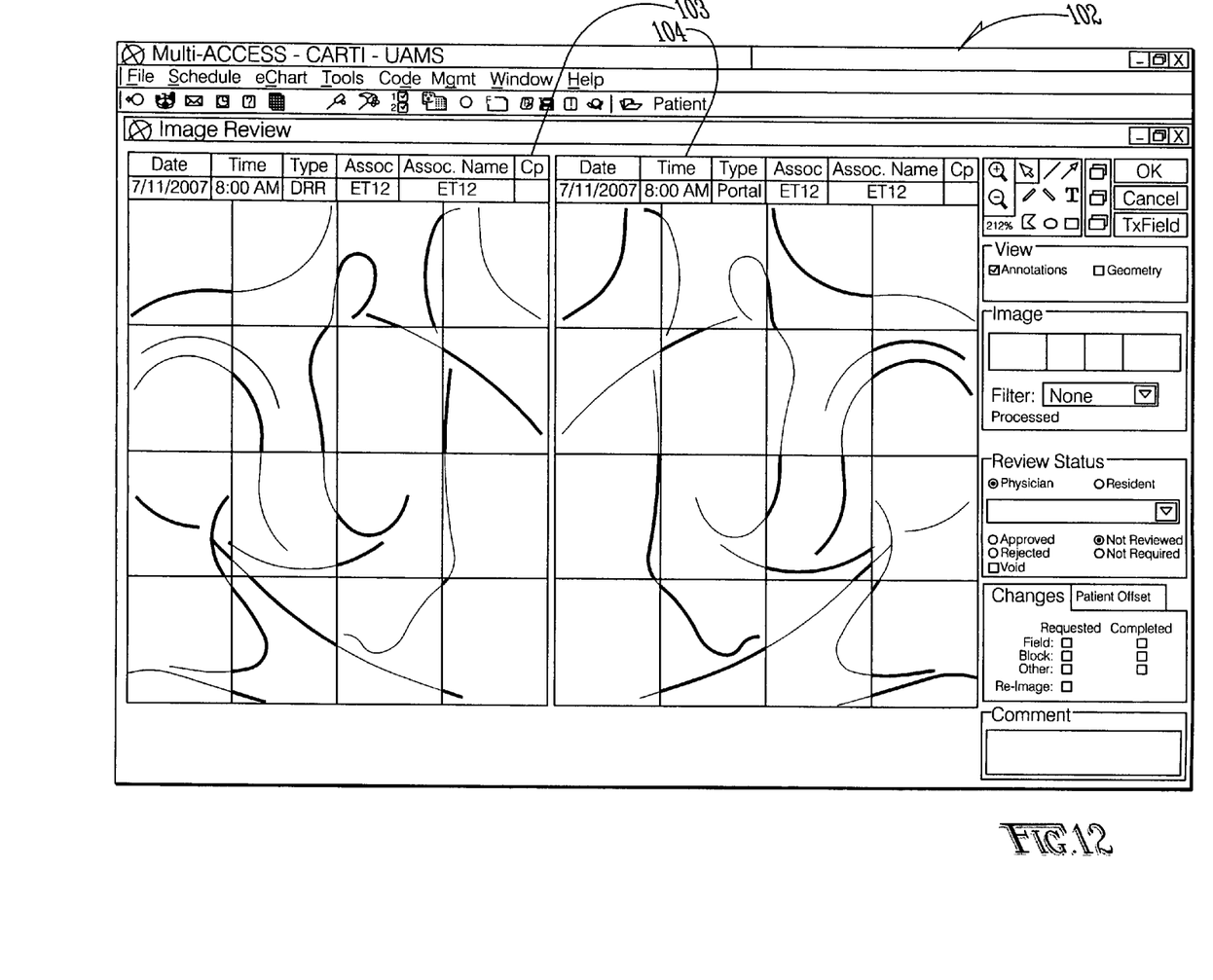
FIG. 12 is a view of fused images of Tube 1 and Tube 2 from FIGS. 10 and 11, respectively. The left image is a fused image from Tube 1 and the right image is a fused image from Tube 2. The DRR image is fused with the corresponding x-ray image in a checkerboard pattern. The upper left square displays the DRR image of that region.

If the user 22 highlights the ET1 Portal, the R&V system 11 will display DRR and Portal images side by side as shown in the window 100 of FIG. 10. The same thing may be done for ET2 Portal as shown in the window 101 of FIG. 11.

In examining the image pairs, it is hard to quantitatively estimate whether or not both images are aligned due to the lack of a reference grid, such as isocenter marks and scale marks. The system 15 provides the user 22 with another useful option: fused images. In the R&V system 11, when the ET12 Portal image is highlighted and reviewed, it appears as shown in the window 102 of FIG. 12. The fused image of Tube 1 is displayed in the left pane 103, and the fused image of Tube 2 is in the right pane 104. The fused images are displayed in a checkerboard pattern.

The system 15 is fully automatic with periodic remote recursive file searching and a auto standby feature when the image source is not accessible. The system 15 provides options for sending raw JPEG images and fused images. It does an auto power-on when the remote IGRT system 10 computer is turned on/off. There is an adjustable pumping interval (5-120 seconds) and an inlet time filter that can be disabled. The receiving DICOM destination server is selectable. Comprehensive logging is provided to facilitate retrospective data collection and analysis. The DICOM server connection may be tested. The working condition indicators are intuitive and a dynamic taskbar icon indicates working status. The application also has an editable field ID.

The present invention has been described with reference to certain preferred and alternative embodiments that are intended to be exemplary only and not limiting to the full scope of the present invention as set forth in the appended claims.

What is claimed is:

1. A device for transferring radiation therapy (RT) images and associated data files over a local area network (LAN) from an image-guided radiation therapy (IGRT) system to a record and verify (R&V) system in a radiation therapy clinic, comprising:
   a data processing device having set of executable instructions residing thereon, wherein the executable instructions instruct the data processing device to perform the following steps:
   (a) selecting an IGRT system as a source of files including x-ray and digitally reconstructed radiograph (ORR) images and associated data files;
   (b) selecting an R&V system as a destination for said images and associated data files;
   (c) probing for the availability of said IGRT system and said R&V system;
   (d) determining whether both said IGRT system and said R&V system are available;
   (e) periodically repeating steps (c) and (d) until both are available;
   (f) scanning files on said IGRT system source;
   (g) selecting files from said IGRT system for automatic transmission based on criteria for selecting said images and associated data files from files stored on said IGRT system for transmission to said R&V system;
   (h) formatting said files for compatibility with the Digital Imaging and Communication in Medicine (DICOM) standard; and
   (i) transmitting said files over the LAN.

2. The device of claim 1, wherein said data processing device is separate from any data processing device associated with said IGRT system.

3. The device of claim 1, wherein said data processing device is associated with said IGRT system.

4. The device of claim 1 where said associated data files comprise patient information and further wherein in step (g) said patient information is transmitted along with said RT images.

5. The device of claim 1 wherein said criteria of step (e) comprise times and dates after a selected time and date.

6. The device of claim 5 wherein said files stored on said IGRT system are stored in a hierarchical arrangement and further wherein said scanning of step (d) comprises the steps of scanning a hierarchical level of files for the most recent date stamp among said files and bypassing lower levels of files associated with less recent date stamps.

7. The device of claim 5 wherein said selected time and date is continually updated based on the image scan to select only the most recent images.

8. The device of claim 1 wherein said RT images are in JPEG format.

9. The device of claim 1 further comprising the step of logging activities to facilitate retrospective data collection and analysis.

* * * * *